(12) United States Patent
Shires et al.

(10) Patent No.: US 7,722,690 B2
(45) Date of Patent: May 25, 2010

(54) METHODS FOR PRODUCING SYNTHESIS GAS

(75) Inventors: Philip Shires, Katy, TX (US); Nicola Salazar, Houston, TX (US); Siva Ariyapadi, Pearland, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

(21) Appl. No.: 11/781,328

(22) Filed: Jul. 23, 2007

(65) Prior Publication Data

US 2008/0081844 A1    Apr. 3, 2008

Related U.S. Application Data

(60) Provisional application No. 60/848,072, filed on Sep. 29, 2006.

(51) Int. Cl.
| | |
|---|---|
| C01B 3/36 | (2006.01) |
| C10J 3/46 | (2006.01) |
| C10J 3/54 | (2006.01) |
| B01J 7/00 | (2006.01) |
| H01M 8/06 | (2006.01) |
| B01J 8/18 | (2006.01) |
| F27B 15/00 | (2006.01) |

(52) U.S. Cl. .................... 48/197 R; 48/61; 422/139
(58) Field of Classification Search ........... 48/197 R
See application file for complete search history.

(56) References Cited

U.S. PATENT DOCUMENTS

| | | | |
|---|---|---|---|
| 4,199,327 A * | 4/1980 | Hempill et al. | ............ 48/202 |
| 4,230,556 A | 10/1980 | Carr et al. | |
| 4,244,706 A | 1/1981 | Forney et al. | |
| 4,257,806 A * | 3/1981 | Fujita et al. | ............ 75/471 |

(Continued)

FOREIGN PATENT DOCUMENTS

IN    P-941118    7/1984

(Continued)

OTHER PUBLICATIONS

Maurstad, Ola. "An Overview of Coal based Integrated Gasification Combined Cycle (IGCC) Technology," Massachusetts Institute for Technolgy—Laboratory for Energy and the Environment, Sep. 2005, MIT LFEE 2005-002 WP, pp. 1-36.

(Continued)

*Primary Examiner*—Alexa D Neckel
*Assistant Examiner*—Matthew J Merkling
(74) *Attorney, Agent, or Firm*—KBR IP Legal

(57) ABSTRACT

A process for producing electrical power, chemicals, carbon dioxide, and hydrogen is provided. One or more feedstocks and one or more oxidants can be combined in a fluidized reaction zone heated to a temperature from about 1050° F. to about 1900° F. to provide a synthesis gas comprising carbon dioxide, carbon monoxide and hydrogen. In one or more embodiments, at least a portion of the synthesis gas can be used as a fuel source for one or more turbines to drive one or more electrical generators. In one or more embodiments, at least a portion of the synthesis gas can be introduced to one or more gas converters to provide methanol, alkyl formates, dimethyl ether, ammonia, Fischer-Tropsch products, derivatives thereof or combinations thereof.

54 Claims, 4 Drawing Sheets

U.S. PATENT DOCUMENTS

| | | | |
|---|---|---|---|
| 4,325,709 A * | 4/1982 | Gohler et al. ............. 48/197 R |
| 4,391,611 A | 7/1983 | Haldipur et al. |
| 4,493,636 A | 1/1985 | Haldipur et al. |
| 5,361,513 A * | 11/1994 | Woessner .................... 34/363 |
| 5,392,594 A | 2/1995 | Moore et al. |
| 5,447,702 A | 9/1995 | Campbell et al. |
| 5,560,900 A * | 10/1996 | Gbordzoe et al. ........... 423/650 |
| 5,578,093 A | 11/1996 | Campbell et al. |
| 5,655,466 A | 8/1997 | Hulkkonen et al. |
| 5,685,138 A | 11/1997 | Rao et al. |
| 5,953,899 A | 9/1999 | Rao et al. |
| 6,054,043 A | 4/2000 | Simpson |
| 6,488,728 B1 * | 12/2002 | Rollinger ............... 48/197 FM |
| 6,676,716 B2 * | 1/2004 | Fujimura et al. ....... 48/197 FM |
| 6,802,178 B2 | 10/2004 | Sprouse et al. |
| 6,966,190 B2 | 11/2005 | Wylie |
| 2003/0131582 A1 * | 7/2003 | Anderson et al. .......... 60/39.55 |
| 2004/0182000 A1 * | 9/2004 | Mansour et al. ........ 48/197 FM |
| 2004/0221583 A1 * | 11/2004 | Wylie .......................... 60/781 |
| 2006/0096298 A1 | 5/2006 | Barnicki et al. |
| 2006/0130719 A1 * | 6/2006 | Morin et al. ................. 110/348 |
| 2006/0149423 A1 | 7/2006 | Barnicki et al. |

FOREIGN PATENT DOCUMENTS

WO  WO 2004065847 A2 *  8/2004

OTHER PUBLICATIONS

"PERP 03/04S11," Coal Gasification Technologies, Nexant Chem Systems, Jan. 2005, pp. 1-46.

Campbell, William M., et al. "Transport Gasifier," U.S. Appl. No. 08/090,804, (Apr. 2008).

Agarwal, A.T., "Improving Rotary Valve Performance," Chemical Eng., Mar. 2005, p. 29-33.

Barker, et al., "Pressure feeder for powered coal or other finely divided solids," I & EC, 43(5), p. 1204-1209, (May 1951).

Alessi, P., et al., "Particle production of steroid drugs using supercritical fluid processing," I&EC Res., 35(12), p. 4718-4726, (Dec. 1996).

"Coal: America's Energy Future, vol. II: A Technical Overview" Report of the National Coal Council, Mar. 2006.

Holt, Neville, "Gasification Process Selection— Trade-offs and Ironies," Electronic Power Research Institute Gasification Technologies Conference, Washington DC, Oct. 4-6, 2004.

* cited by examiner

METHODS FOR PRODUCING SYNTHESIS GAS

CROSS-REFERENCE TO RELATED APPLICATIONS

This application claims benefit of U.S. Provisional Patent Application No. 60/848,072, filed on Sep. 29, 2006.

FIELD

The present embodiments generally relate to the gasification of hydrocarbons. More particularly, embodiments of the present invention relate to the gasification of coal based feedstocks, waste polymer materials, and/or biomass materials.

BACKGROUND

Gasification is a high-temperature process usually conducted at elevated pressure to convert carbon-containing materials into carbon monoxide and hydrogen gas. Since this gas is often used for the synthesis of chemicals or synthetic hydrocarbon fuels, the gas is often referred to as "synthesis gas" or, more succinctly "syngas". Syngas can be used as a fuel to generate electricity or steam and as a source of hydrogen.

Typical feeds to gasification include petroleum-based materials that are neat or residues of processing materials, such as heavy crude oil, bitumen recovered from tar sands, kerogen from oil shale, coke, and other high-sulfur and/or high metal-containing residues; gases; and various carbonaceous waste materials. Dry or slurried feedstock is reacted in the gasifier in a reducing (oxygen-starved) atmosphere at high temperature and (usually) high pressure. The resulting syngas typically contains about 85 percent of the feed carbon content as carbon monoxide, with the balance being a mixture of carbon dioxide and methane.

Three basic types of gasifiers are: fixed bed, fluidized bed and entrained flow. The fixed bed gasifier is operated at relatively low outlet temperature (425° C.-600° C.) and requires a lesser amount of oxygen compared to the other two types of gasifiers; however, the product syngas contains substantial unconverted methane, and by-product tars and oils. The fluidized bed gasifier operates at more moderate outlet temperatures (900° C.-1050° C.) and requires a greater amount of oxygen than a comparable fixed bed gasifier. While the synthesis gas from a fluidized bed gasifier is of higher purity, the carbon conversion is lower than a comparable entrained flow gasifier which operates at much higher temperatures (1250° C.-1600° C.) and requires significantly higher energy input, but from which synthesis gas of the highest purity can be obtained.

The high temperature in the entrained gasifiers and in the lower zones of certain fixed bed gasifiers converts the inorganic materials in the feed into a molten vitrified material which solidifies when removed from the gasifier, producing a material resembling coarse sand and generally referred to as slag. Fluid bed gasifiers produce dry ash which is not vitrified but only consolidated or agglomerated. Depending on the gasifier, it is desirable either to remove ash at lower temperatures (non-slagging gasifiers) or as a low viscosity liquid at high temperatures (slagging gasifiers). This inert slag or ash has a variety of uses in the construction and building industries.

The raw syngas can be treated using proven commercial technologies to remove trace elements and other impurities for recovery or recycle to the gasifier. Sulfur can be recovered as marketable elemental sulfur or sulfuric acid. In addition to a fuel source, syngas can be used as a raw material in the production of fuels, chemicals, fertilizers, and industrial gases.

BRIEF DESCRIPTION OF THE DRAWINGS

So that the manner in which the above recited features of the present embodiments can be understood in detail, a more particular description of the invention, briefly summarized above, may be had by reference to embodiments, some of which are illustrated in the appended drawings. The appended drawings illustrate only typical embodiments and are therefore not to be considered limiting of its scope, for the inventions herein may admit to other equally effective embodiments.

Figure 1:
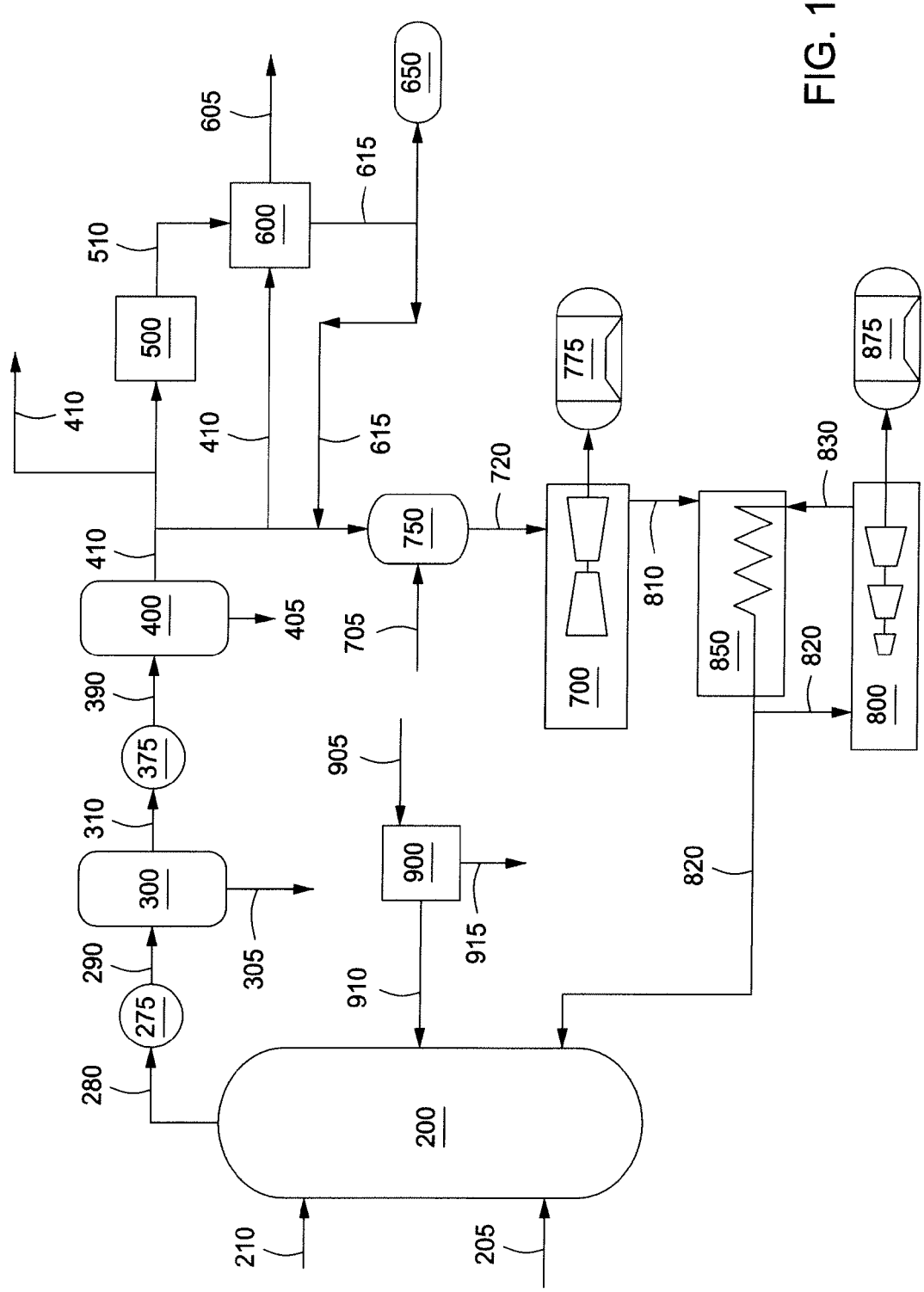
FIG. 1 depicts an illustrative gasification system according to one or more embodiments.

The present embodiments are detailed below with reference to the listed Figures.

DETAILED DESCRIPTION OF THE EMBODIMENTS

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

In one or more embodiments, a gasification system and process for converting feedstock to a synthesis gas or simply "syngas" is provided. The gasification systems and processes as described provide an excellent balance in flexibility, efficiency and safety with low to no emissions. The systems and processes can produce a syngas stream having reduced impurities, reduced oxygen consumption, and higher cold-gas efficiency. The syngas produced can be further processed into marketable products including but not limited to electricity, fuels, chemicals, steam, and hydrogen.

In one or more embodiments, one or more feedstocks and one or more oxidants can be combined in a fluidized reaction zone. One or more sorbents are optional. The reaction zone can be heated to a temperature of from 1050° F. to 1900° F. (i.e. relatively low temperature) to provide a synthesis gas comprising carbon dioxide, carbon monoxide, and hydrogen. At least a portion of the synthesis gas can be passed or fed to one or more gas or combustion turbines to generate power and/or electricity. At least a portion of the synthesis gas can be passed to one or more gas converters to produce one or more Fischer-Tropsch products, chemicals, and/or feedstocks methanol, derivatives thereof, and/or combinations thereof, including ammonia and methanol.

In one or more embodiments, the source of hydrogen and carbon monoxide to the gasifier is from the gasification process itself. In one or more embodiments, the hydrogen and carbon monoxide can be independently fed to the gasifier on demand. In one or more embodiments, a second material can be used to scavenge oxygen entering the gasifier, for example during interruptions in gasifier feed, thereby preventing the oxygen concentration from building to a level sufficient to support uncontrolled reactions with the hydrogen present in the gasifier. In one or more embodiments, the second material can include an ash containing reactive carbon which can scavenge residual oxygen.

FIG. 1 depicts an illustrative gasification system according to one or more embodiments. In one or more embodiments, the gasification system can include one or more gasifiers 200, particulate removal systems 300, and gas purification systems 400 to produce a synthesis gas ("syngas") stream 410 comprising 85% or more of combined carbon monoxide and hydrogen with the balance being primarily carbon dioxide and methane. In one or more embodiments, the gasification system can include one or more gas converters 500 to produce one or more Fischer-Tropsch products, chemicals, and/or feedstocks, derivatives thereof, and/or combinations thereof, including ammonia and methanol. In one or more embodiments, the gasification system can include one or more hydrogen separators 600, fuel cells 650, combustion turbines 700, combustors 750, steam turbines 800, waste heat boilers 850, and generators 775, 875 to produce fuel, power, steam and/or energy. In one or more embodiments, the gasification system can include one or more air separation units ("ASU") 900 for the production of essentially nitrogen-free synthesis gas.

One or more feedstocks via stream 210 and one or more oxidants via stream 205 can be introduced to the one or more gasifiers 200 to produce a raw syngas stream 280. In one or more embodiments, the type and amount of oxidant can determine the composition and physical properties of the syngas and hence, the downstream products made therefrom. The one or more oxidants can include but are not limited to air; oxygen; essentially oxygen; oxygen-enriched air; mixtures of oxygen and air; mixtures of oxygen and inert gas such as nitrogen and argon; and the like. In one or more embodiments, the oxidant can contain about 65% volume oxygen or more, or about 70% volume oxygen or more, or about 75% volume oxygen or more, or about 80% volume oxygen or more, or about 85% volume oxygen or more, or about 90% volume oxygen or more, or about 95% volume oxygen or more, or about 99% volume oxygen or more. As used herein, the term "essentially oxygen" refers to an oxygen stream containing 51 vol. % oxygen or more. As used herein, the term "oxygen-enriched air" refers to air containing 21 vol. % oxygen or more. Oxygen-enriched air can be obtained, for example, from cryogenic distillation of air, pressure swing adsorption, membrane separation or any combination thereof.

In one or more embodiments, the oxidant stream 205 can be nitrogen-free or essentially nitrogen-free. By "essentially nitrogen-free," it is meant that the oxidant stream 205 contains about 5 vol. % nitrogen or less, 4 vol. % nitrogen or less, 3 vol. % nitrogen or less, 2 vol. % nitrogen or less, or 1 vol. % nitrogen or less.

The term "feedstock" as used herein refers to a raw material, whether solid, gas or liquid. For example, the feedstock can include one or more carbonaceous materials. In one or more embodiments, the carbonaceous materials can include but are not limited to biomass (i.e., plant and/or animal matter or plant and/or animal derived matter); coal (high-sodium and low-sodium lignite, lignite, subbituminous, and/or anthracite, for example); oil shale; coke; tar; asphaltenes; low ash or no ash polymers; hydrocarbon-based polymeric materials; biomass derived material; or by-product derived from manufacturing operations. The hydrocarbon-based polymeric materials can include, for example, thermoplastics, elastomers, rubbers, including polypropylenes, polyethylenes, polystyrenes, including other polyolefins, homo polymers, copolymers, block copolymers, and blends thereof; PET (polyethylene terephthalate), poly blends, poly-hydrocarbons containing oxygen; heavy hydrocarbon sludge and bottoms products from petroleum refineries and petrochemical plants such as hydrocarbon waxes; blends thereof, derivatives thereof, and combinations thereof.

In one or more embodiments, the feedstock can include a mixture or combination of two or more carbonaceous materials (i.e. carbon-containing materials). In one or more embodiments, the feedstock can include a mixture or combination of two or more low ash or no ash polymers, biomass derived materials, or by-products derived from manufacturing operations. In one or more embodiments, the feedstock can include one or more carbonaceous materials combined with one or more discarded consumer products, such as carpet and/or plastic automotive parts/components including bumpers and dashboards. Such discarded consumer products are preferably suitably reduced in size to fit within the gasifier 200. In one or more embodiments, the feedstock can include one or more recycled plastics such as polypropylene, polyethylene, polystyrene, derivatives thereof, blends thereof, or any combination thereof. Accordingly, the process can be useful for accommodating mandates for proper disposal of previously manufactured materials.

In one or more embodiments, the feedstock steam 210 can be a dry feed or conveyed to the gasifier 200 as a slurry or suspension. In one or more embodiments, the feedstock can be dried, for example to 18% moisture, and then pulverized by milling units such as one or more parallel bowl mills prior to feeding to the gasifier 200. In one or more embodiments, the feedstock can have an average particle diameter size of from about 50 microns to about 500 microns, or from about 50 microns to about 400 microns. In one or more embodiments, the average particle diameter size of the feedstock can range from about 150 microns to about 450 microns, or from about 250 microns to about 400 microns.

The raw syngas stream 280 exits the one or more gasifiers 200. The raw syngas stream 280 can contain 85% or more carbon monoxide and hydrogen with the balance being primarily carbon dioxide and methane. In one or more embodiments, the raw syngas stream 280 can contain 90% or more carbon monoxide and hydrogen, 95% or more carbon monoxide and hydrogen, 97% or more carbon monoxide and hydrogen, or 99% or more carbon monoxide and hydrogen. In one or more embodiments, the carbon monoxide content of the raw syngas stream 280 can range from a low of about 10 vol %, 20 vol %, or 30 vol % to a high of about 50 vol %, 70 vol % or 85 vol %. In one or more embodiments, the carbon monoxide content of the raw syngas stream 280 can range from a low of about 15 vol %, 25 vol %, or 35 vol % to a high of about 65 vol %, 75 vol % or 85 vol %. In one or more embodiments, the hydrogen content of the raw syngas stream 280 can range from a low of about 1 vol %, 5 vol %, or 10 vol % to a high of about 30 vol %, 40 vol % or 50 vol %. In one or more embodiments, the hydrogen content of the raw syngas stream 280 ranges from about 20 vol % to about 30 vol %.

In one or more embodiments, the raw syngas stream 280 can contain less than 25 vol % of combined nitrogen, methane, carbon dioxide, water, hydrogen sulfide, and hydrogen chloride. In one or more embodiments, the raw syngas stream 280 can contain less than 20 vol % of combined nitrogen, methane, carbon dioxide, water, hydrogen sulfide, and hydrogen chloride. In one or more embodiments, the raw syngas stream 280 can contain less than 15 vol % of combined nitrogen, methane, carbon dioxide, water, hydrogen sulfide, and hydrogen chloride. In one or more embodiments, the raw syngas stream 280 can contain less than 10 vol % of combined nitrogen, methane, carbon dioxide, water, hydrogen sulfide, and hydrogen chloride. In one or more embodiments, the raw syngas stream 280 can contain less than 5 vol % of combined nitrogen, methane, carbon dioxide, water, hydrogen sulfide, and hydrogen chloride.

In one or more embodiments, the carbon dioxide content of the raw syngas stream 280 is about 25 vol % or less, 20 vol % or less, 15 vol % or less, 10 vol % or less, 5 vol % or less, 3 vol % or less, 2 vol % or less, or 1 vol % or less. In one or more embodiments, the methane content of the raw syngas stream 280 is about 15 vol % or less, 10 vol % or less, 5 vol % or less, 3 vol % or less, 2 vol % or less, or 1 vol % or less. In one or more embodiments, the water content of the raw syngas stream 280 is about 40 vol % or less, 30 vol % or less, 25 vol % or less, 20 vol % or less, 15 vol % or less, 10 vol % or less, 5 vol % or less, 3 vol % or less, 2 vol % or less, or 1 vol % or less. In one or more embodiments, the raw syngas stream 280 is nitrogen-free or essentially nitrogen-free, e.g. containing less than 0.5 vol % nitrogen.

One or more particulate removal systems 300 can be used to partially or completely remove any particulates from the raw syngas stream 280 to provide a particulate stream 305 and a separated syngas stream 310. In one or more embodiments, the raw syngas stream 280 can be cooled using one or more coolers 275 ("primary coolers") to provide a cooled raw syngas stream 290 prior to entry into the particulate removal systems 300. For example, the raw syngas stream 280 can be cooled to about 1,000° F. or less. In one or more embodiments, the raw syngas stream 280 can be cooled to about 900° F. or less, 800° F. or less, 700° F. or less, 600° F. or less, 500° F. or less, 400° F. or less, or 300° F. or less. In one or more embodiments, cooling the raw syngas stream 280 prior to the one or more particulate removal systems 300 is optional. For example, the raw syngas stream 280 can be fed directly to the particulate removal systems 300, resulting in hot gas particulate removal (e.g. 1050° F.-1900° F.).

The one or more particulate removal systems 300 can include one or more separation devices such as conventional disengagers and/or cyclones (not shown). Particulate control devices ("PCD") capable of providing an outlet particulate concentration below the detectable limit of about 0.1 ppmw can also be used. Illustrative PCDs can include but are not limited to sintered metal filters, metal filter candles, and/or ceramic filter candles (for example, iron aluminide filter material).

The solid particulates from stream 305 can be recycled to the gasifier 200 (not shown) or purged from the system, as shown. The separated syngas stream 310 can be cooled using one or more coolers 375 ("secondary coolers") to provide a cooled, separated syngas stream 390. The separated syngas stream 390 can have a temperature of about 650° F. or less, such as 300° F. to 550° F. The cooled, separated syngas stream 390 can be treated within one or more gas purification systems 400 to remove contaminants and to provide a waste stream 405, and a treated syngas stream 410. The one or more gas purification systems 400 can include systems, processes or devices to remove sulfur and/or sulfur containing compounds in the separated syngas stream 390. Illustrative catalytic gas purification systems 400 can include, but are not limited to, systems using zinc titanate, zinc ferrite, tin oxide, zinc oxide, iron oxide, copper oxide, cerium oxide or mixtures thereof. Illustrative process-based gas purification systems 400 can include, but are not limited to, the Selexol™ process, the Rectisol® process, the CrystaSulf® process, and the Sulfinol® Gas Treatment Process.

In one or more embodiments, one or more amine solvents such as methyl-diethanolamine (MDEA) can be used to remove any acid gas from the syngas stream 390. Physical solvents such as Selexol (dimethyl ethers of polyethylene glycol) or Rectisol® (cold methanol), can also be used. If the syngas stream 390 contains carbonyl sulfide (COS), the carbonyl sulfide can be converted by hydrolysis to hydrogen sulfide by reaction with water over a catalyst and then absorbed using the methods described above. If the syngas stream 390 contains mercury, the mercury can be removed using a bed of sulfur-impregnated activated carbon.

In one or more embodiments, a cobalt-molybdenum ("Co—Mo") catalyst can be incorporated into the one or more treatment units 400 to perform a sour shift conversion of the syngas. The Co—Mo catalyst can operate at a temperature of about 550° F. in presence of H2S, such as about 100 ppmw H2S. If Co—Mo catalyst is used to perform a sour shift, subsequent downstream removal of sulfur can be accomplished using any of the above described sulfur removal methods and/or techniques.

The resulting treated syngas stream 410 from the gas purification system 400 can be combusted to produce or generate power and/or steam. In one or more embodiments, the treated syngas stream 410 can be sold as a commodity. In one or more embodiments, the treated syngas stream 410 can be used to produce Fischer-Tropsch products, chemicals, and/or feedstocks. In one or more embodiments, hydrogen can be separated from the treated syngas stream 410 and used in hydrogenation processes, fuel cell energy processes, ammonia production, and as a fuel. In one or more embodiments, carbon monoxide can be separated from the treated syngas stream 410 and used for the production of chemicals, such as acetic acid, phosgene/isocyanates, formic acid, and propionic acid.

Still referring to FIG. 1, the one or more gas converters 500 can be used to convert the treated syngas stream 410 into one or more Fischer-Tropsch products, chemicals, and/or feedstocks via stream 510 ("converted gas stream 510"). In one or more embodiments, at least one of the one or more gas converters 500 can include one or more shift reactors to adjust the hydrogen to carbon monoxide ratio (H2:CO) of the synthesis gas by converting CO to CO2. Within the one or more shift reactors, a water-gas shift reaction reacts at least a portion of the carbon monoxide in the treated syngas stream 410 with water in the presence of a catalyst and/or a high temperature to produce hydrogen and carbon dioxide. The one or more shift reactors can include, but are not limited to, single stage adiabatic fixed bed reactors; multiple-stage adiabatic fixed bed reactors with interstage cooling, steam generation or cold quench reactors; tubular fixed bed reactors with steam generation or cooling; fluidized bed reactors, or any combination thereof. In one or more embodiments, a sorption enhanced water-gas shift (SEWGS) process, utilizing a pressure swing adsorption unit having multiple fixed bed reactors packed with shift catalyst and high temperature (around 900° F.) carbon dioxide adsorbent, can be used. Various shift catalysts can be employed.

In at least one specific embodiment, the shift reactors can include two reactors arranged in series. A first reactor can be operated at high temperature (about 650° F. to about 750° F.)

to convert a majority of the CO present in the treated syngas stream 410 to CO2 at a relatively high reaction rate using an iron-chrome catalyst. A second reactor can be operated at a relatively low temperature (about 300° F. to about 400° F.) to complete the conversion of CO to CO2 using a mixture of copper oxide and zinc oxide.

In one or more embodiments, the recovered carbon dioxide from the shift reactors 500 can be used in a fuel recovery process to enhance the recovery of oil and gas. In an illustrative oil recovery process, carbon dioxide can be injected and flushed into an area beneath an existing well where "stranded" oil exists. The water and carbon dioxide removed with the crude oil can then be separated and recycled.

In one or more embodiments, at least one of the one or more gas converters 500 can be used to produce one or more Fischer-Tropsch ("F-T") products, including refinery/petrochemical feedstocks, transportation fuels, synthetic crude oil, liquid fuels, lubricants, alpha olefins, waxes, and so on. The reaction can be carried out in any type reactor, e.g., fixed bed, moving bed, fluidized bed, slurry, bubbling bed, etc using copper, ruthenium, iron or cobalt based catalysts, or combination thereof, under conditions ranging from about 190° C. to about 450° C. depending on the reactor configuration. Additional reaction and catalyst details can be found in U.S. Patent Application No. 20050284797 and U.S. Pat. Nos.: 5,621,155; 6,682,711; 6,331,575; 6,313,062; 6,284,807; 6,136,868; 4,568,663; 4,663,305; 5,348,982; 6,319,960; 6,124,367; 6,087,405; 5,945,459; 4,992,406; 6,117,814; 5,545,674 and 6,300,268.

The F-T products are liquids which can be shipped to a refinery site for further chemically reacting and upgrading to a variety of products. Certain products, e.g. C4-C5 hydrocarbons, can be high quality paraffin solvents which, if desired, can be hydrotreated to remove olefin impurities, or employed without hydrotreating to produce a wide variety of wax products. C16+liquid hydrocarbon products can be upgraded by various hydroconversion reactions, e.g., hydrocracking, hydroisomerization catalytic dewaxing, isodewaxing, etc. or combinations thereof, to produce mid-distillates, diesel and jet fuels such as low freeze point jet fuel, high cetane jet fuel, etc. isoparaffinic solvents, lubricants, e.g., lube oil blending components and lube oil base stocks suitable for transportation vehicles, non-toxic drilling oils suitable for use in drilling muds, technical and medicinal grade white oil, chemical raw materials, and various specialty products.

In at least one specific embodiment, at least one of the one or more gas converters 500 can include one or more slurry bubble column reactors to produce one or more F-T products. The slurry bubble column reactors can operate at a temperature of less than 220° C. and from about 10 to about 600 psia, or about 250 to about 350 psia using a cobalt catalyst promoted with rhenium and supported on titania having a Re:Co weight ratio in the range of about 0.01 to about 1 and containing from about 2% wt to about 50% wt cobalt. In one or more embodiments, the catalyst within the slurry bubble column reactors can include, but is not limited to, a titania support impregnated with a salt of a catalytic copper or an Iron Group metal, a polyol or polyhydric alcohol and, optionally, a rhenium compound or salt. Examples of polyols or polyhydric alcohols include glycol, glycerol, derythritol, threitol, ribitol arabinitol, xylitol, allitol, dulcitol, gluciotol, sorbitol, and mannitol. The catalytic metal, copper or Iron Group metal as a concentrated aqueous salt solution, for example cobalt nitrate or cobalt acetate, can be combined with the polyol and optionally perrhenic acid while adjusting the amount of water to obtain 15 wt % cobalt in the solution and using optionally incipient wetness techniques to impregnate the catalyst onto rutile or anatase titania support, optionally spray-dried and calcined. This method reduces the need for rhenium promoter. Additional details can be found in U.S. Pat. Nos. 5,075,269 and 6,331,575.

In one or more embodiments, at least one of the one or more gas converters 500 can be used to produce methanol, alkyl formates, dimethyl ether, ammonia, acetic anhydride, acetic acid, methyl acetate, acetate esters, vinyl acetate and polymers, ketenes, formaldehyde, dimethyl ether, olefins, derivatives thereof, and/or combinations thereof. For methanol production, for example, the Liquid Phase Methanol Process can be used (LPMEOH™). In this process, the carbon monoxide in the syngas stream 410 can be directly converted into methanol using a slurry bubble column reactor and catalyst in an inert hydrocarbon oil reaction medium which can conserve heat of reaction while idling during off-peak periods for a substantial amount of time while maintaining good catalyst activity. Additional details can be found in U.S. Patent Application No. 2006/0149423 and prior published Heydorn, E. C., Street, B. T., and Kornosky, R. M., "Liquid Phase Methanol (LPMEOH™) Project Operational Experience," (Presented at the Gasification Technology Council Meeting in San Francisco on Oct. 4-7, 1998). Gas phase processes for producing methanol can also be used. For example, known processed using copper based catalysts, the Imperial Chemical Industries process, the Lurgi process and the Mitsubishi process can be used.

For ammonia production, at least one of the one or more gas converters 500 can be adapted to operate the Haber-Bosch process described in LeBanc et al in "Ammonia," Kirk-Othmer Encyclopedia of Chemical Technology, Volume 2, 3rd Edition, 1978, pp., 494-500. For alkyl formate production, such as for example, methyl formate, any of several processes wherein carbon monoxide and methanol are reacted in either the liquid or gaseous phase in the presence of an alkaline catalyst or alkali or alkaline earth metal methoxide catalyst can be used. Additional details can be found in U.S. Pat. Nos.: 3,716,619; 3,816,513; and 4,216,339.

Although not shown in FIG. 1, carbon dioxide can be separated and/or recovered from the converted gas stream 510. In one or more embodiments, physical adsorption techniques can be used. Suitable adsorbents and techniques include, but are not limited to, propylene carbonate physical adsorbent solvent as well as other alkyl carbonates, dimethyl ethers of polyethylene glycol of two to twelve glycol units (Selexol™ process), n-methyl-pyrrolidone, sulfolane, use of the Sulfinol® Gas Treatment Process.

At least a portion of the converted gas stream 510 can be sold or upgraded using further downstream processes not shown. In one or more embodiments, at least a portion of the converted gas stream 510 can be directed to the one or more hydrogen separators 600. In one or more embodiments, at least a portion of the treated syngas stream 410 can bypass the one or more gas converters 500 described above, and can be fed directly to the one or more hydrogen separators 600.

The one or more hydrogen separators 600 can include any system or device to selectively separate hydrogen from syngas to provide one or more purified hydrogen streams and one or more waste gas streams. In one or more embodiments, the hydrogen separators 600 can provide a carbon dioxide rich stream 605, and a hydrogen rich stream 615. In one or more embodiments, at least a portion of the hydrogen rich stream 615 can be used as a feedstock to one or more fuel cells 650, and at least a portion of the hydrogen rich stream 615 can be combined with the treated syngas stream 410 prior to use as a fuel in the one or more combustors 750. In one or more embodiments, the hydrogen separators 600 can utilize pressure swing absorption, cryogenic distillation, and semi-permeable membranes. Suitable absorbents can include caustic soda, potassium carbonate or other inorganic bases, and/or alanolamines.

In one or more embodiments, at least a portion of the treated syngas stream 410 can be combusted in one or more combustors 750 to provide a high pressure/high temperature exhaust gas stream 720. In one or more embodiments, the exhaust gas stream 720 can be introduced to one or more combustion turbines 700 to provide an exhaust gas stream 810 and mechanical shaft power to drive the one or more electric generators 775. In one or more embodiments, the exhaust gas stream 810 can be introduced to one or more heat recovery systems 850 to provide steam via stream 820. In one or more embodiments, a first portion of the steam in stream 820 can be introduced to one or more steam turbines 800 to provide mechanical shaft power to drive one or more electric generators 875. In one or more embodiments, a second portion of the steam within stream 820 can be introduced to the gasifier 200, and/or other auxiliary process equipment. In one or more embodiments, lower pressure steam from the one or more steam turbines 800 can be recycled to the one or more heat recovery systems 850 via stream 830.

In one or more embodiments, pure oxygen from the ASU 900 can be supplied to the gasifier 200. In one or more embodiments, the ASU 900 can provide a nitrogen-lean and oxygen-rich stream 910 to the one or more gasifiers 200, thereby minimizing the nitrogen concentration in the system. The use of a nearly pure oxygen stream allows the gasifier 200 to produce a syngas stream 280 that is essentially nitrogen-free, e.g. containing less than 0.5% nitrogen/argon. In one or more embodiments, the ASU 900 can be a high-pressure, cryogenic type separator, which can be supplemented with air via stream 905. The reject nitrogen stream 915 from the ASU can be added to a combustion turbine, as explained in more detail below or used as utility.

In one or more embodiments, up to 50% of the total oxidant fed to the gasifier 200 can be supplied by the ASU 900 via stream 910. In one or more embodiments, up to 40% of the total oxidant fed to the gasifier 200 can be supplied by the ASU 900 via stream 910. In one or more embodiments, up to 30% of the total oxidant fed to the gasifier can be supplied by the ASU 900 via stream 910. In one or more embodiments, up to than 20% of the total oxidant fed to the gasifier can be supplied by the ASU 900 via stream 910. In one or more embodiments, up to than 10% of the total oxidant fed to the gasifier can be supplied by the ASU 900 via stream 910.

Figure 2:
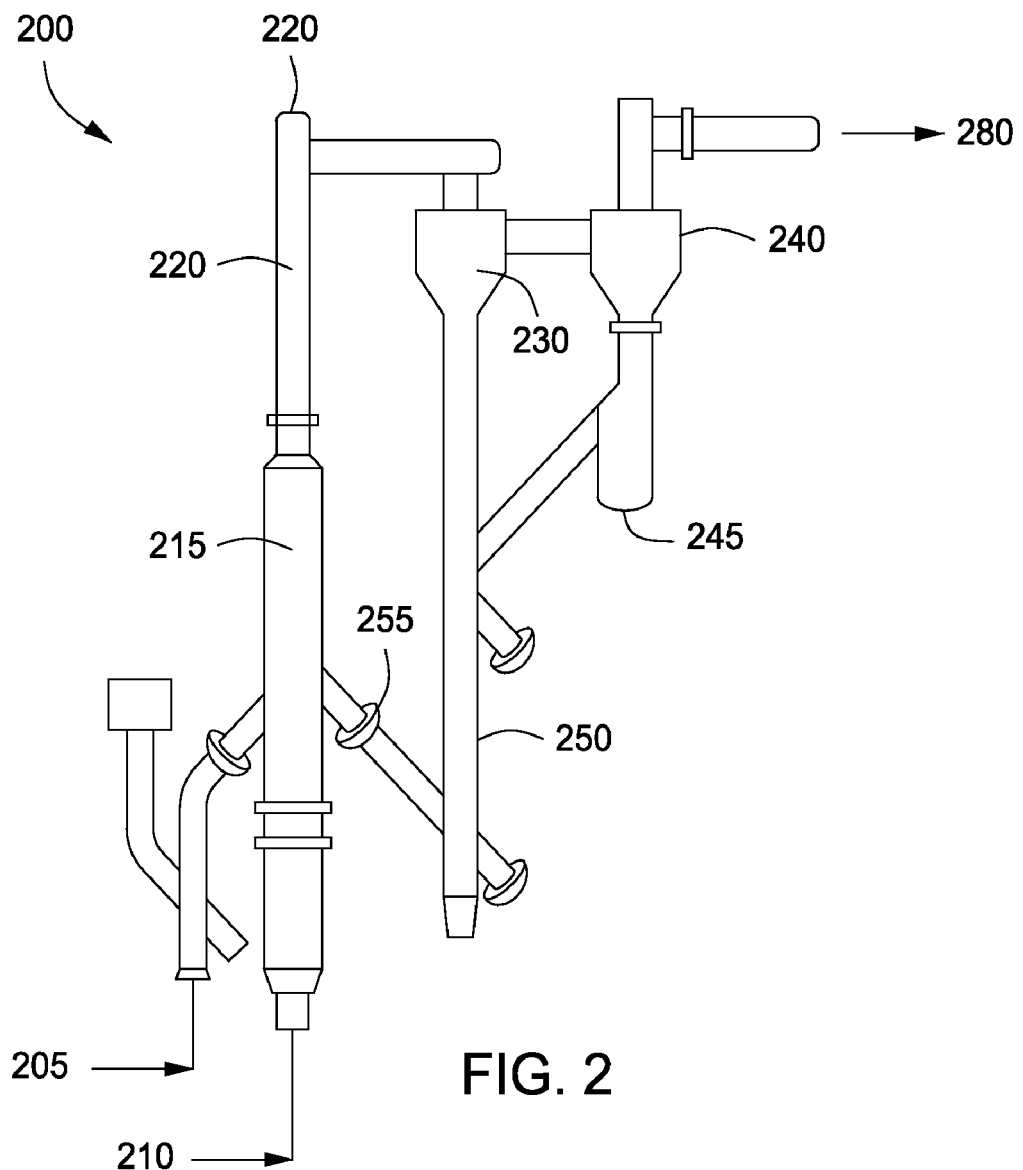
FIG. 2 depicts an illustrative gasifier according to one or more embodiments.

FIG. 2 depicts an illustrative gasifier according to one or more embodiments. The gasifier 200 can include a single reactor train or two or more reactor trains arranged in series or parallel. Each reactor train can include one or more mixing zones 215, risers 220, and disengagers 230, 240. Each reactor train can be configured independent from the others or configured where any of the one or more mixing zones 215, risers 220, disengagers 230, 240 can be shared. For simplicity and ease of description, embodiments of the gasifier 200 will be further described in the context of a single reactor train.

In one or more embodiments, the one or more feedstocks (via stream 210) and one or more oxidants (via stream 205) can be combined in the mixing zone 215 to provide a gas mixture. In one or more embodiments, the feedstock and oxidant can be injected separately, as shown, to the mixing zone 215 or mixed prior to injection into the mixing zone (not shown). In one or more embodiments, the feedstock and oxidant can be injected sequentially into the gasifier 200. In one or more embodiments, the feedstock and oxidant can be injected simultaneously into the gasifier 200. Feed (i.e. introduction of the feedstock and oxidant) to the gasifier 200 can be continuous or intermittent depending on desired product types and grades.

The gas suspension moves upward through the mixing zone 215 into the riser 220 where additional residence time allows the char gasification, methane/steam reforming, tar cracking, and/or water-gas shift reactions to occur. The riser 220 can operate at a higher temperature than the mixing zone 215, and can have a smaller diameter than the mixing zone 215. In one or more embodiments, the superficial gas velocity in the riser 220 can range from about 10 ft/s to about 90 ft/s, or from about 20 ft/s to about 80 ft/s, or from about 30 ft/s to about 70 ft/s, or from about 30 ft/s to about 40 ft/s, or from about 35 ft/s to about 60 ft/s. Suitable temperatures in the riser 220 can range from about 600° F. to about 2,000° F.

The gas mixture exits the riser 220 and enters the disengagers 230, 240 where the larger particulates can be separated from the gas and recycled back to the mixing zone 215 via one or more conduits, including, but not limited to, a standpipe 250, and/or j-leg 255. The j-leg 255 can include a non-mechanical "j-valve" to increase the effective solids residence time, increase the carbon conversion, and minimize aeration requirements for recycling solids to the mixing zone 215. In one or more embodiments, the disengagers 230, 240 can be cyclones. In one or more embodiments, one or more particulate transfer devices 245, such as one or more loop seals, can be located downstream of the disengagers 230, 240 to collect separated particulate fines. Any entrained or residual particulates in the raw syngas stream 280 can be removed using the one or more particulate removal systems 300 (shown in FIG. 1).

In one or more embodiments, the average particle diameter size of the feedstock can be used as a control variable to optimize particulate density of the solids recycled to the mixing zone via the standpipe 250. In one or more embodiments, the feedstock particle size can be varied to optimize the particulate mass circulation rate, and to improve the flow characteristics of the gas mixture within the mixing zone 215 and riser 220.

One or more sorbents can also be added to the gasifier 200. In one or more embodiments, the sorbents can be added to capture contaminants from the syngas, such as sodium vapor in the gas phase within the gasifier 200. In one or more embodiments, the sorbents can be added to scavenge oxygen at a rate and level sufficient to delay or prevent the oxygen from reaching a concentration that can result in undesirable side reactions with hydrogen (e.g. water) from the feedstock within the mixing zone 215. In one or more embodiments, the sorbents can be used to dust or coat feedstock particles in the gasifier to reduce the tendency for the particles to agglomerate. In one or more embodiments, the one or more oxidants can be introduced at the bottom of the mixing zone 215 to increase the temperature within the mixing zone 215 and riser 220 by combusting any carbon contained within the recirculated particulates to form an ash ("char"). In one or more embodiments, the sorbents can be ground to an average particle size of about 5 μm to about 100 microns, or about 10 microns to about 75 microns. Illustrative sorbents can include but are not limited to carbon rich ash, limestone, dolomite, and coke breeze. Residual sulfur released from the feedstock can be captured by native calcium in the feed or by a calcium based sorbent to form calcium sulfide.

In one or more embodiments, the one or more oxidants can be introduced into the mixing zone 215 at a rate suitable to control the temperature of the mixing zone 215. In one or more embodiments, the one or more oxidants can include excess air. In one or more embodiments, the one or more oxidants can be sub-stoichiometric air wherein the molar ratio of oxygen to carbon can be maintained at a sub-stoichiometric concentration to favor the formation of carbon monoxide over carbon dioxide in the mixing zone 215. In one or more embodiments, the oxygen supplied via the oxidant to the mixing zone 215 can be less than five percent of the stoichiometric amount of oxygen required for complete combustion of all the carbon supplied to the mixing zone 215. Excess oxygen and steam in the air can be consumed by the recirculating solids stabilizing reactor temperature during operation and periods of feed interruption if any.

The residence time and temperature in the gasifier 200 should be sufficient for water-gas shift reaction to reach equilibrium. In one or more embodiments, the residence time of the feedstock in the mixing zone 215 is greater than about 2 seconds. In one or more embodiments, the residence time of the feedstock in the mixing zone 215 is greater than about 5 seconds. In one or more embodiments, the residence time of the feedstock in the mixing zone 215 is greater than about 10 seconds. In one or more embodiments, the operating temperature of the gasifier 200 ranges from about 500° F., 750° F., or 1,000° F. to about 1,200° F., 1500° F., or 1800° F. In one or more embodiments, the operating temperature of the gasifier 200 ranges from about 700° F. to about 1750° F. In one or more embodiments, the operating temperature of the gasifier 200 ranges from about 900° F. to about 1600° F. In one or more embodiments, the operating temperature of the gasifier 200 ranges from about 1,200° F. to about 1600° F.

In one or more embodiments, the gasifier 200 can be operated in a temperature range sufficient to not melt the ash, such as from about 1050° F. to about 1900° F., or from about 1540° F. to about 1710° F. Heat can be supplied by burning the carbon in the recirculated solids in the lower part of the mixing zone 215 before recirculated solids contact the entering feedstock. In one or more embodiments, startup can be initiated by bringing the mixing zone 215 to a temperature from about 950° F. to about 1200° F. and optionally by feeding coke breeze or the equivalent to the mixing zone 215 to further increase the temperature of the mixing zone 215 to about 1650° F.

In one or more embodiments, the operating temperature of the gasifier 200 can be controlled by the recirculation rate and residence time of the solids within the riser 220; by reducing the temperature of the ash prior to recycle to the mixing zone 215; by the addition of steam to the mixing zone 215; and/or by the addition of oxidant to the mixing zone 215. The recirculating solids also can serve to rapidly heat the incoming feedstock which also minimizes tar formation.

In one or more embodiments, the mixing zone 215 can be operated at pressures from about 0 psig to about 650 psig to increase thermal output per unit reactor cross-sectional area and enhance energy output in any subsequent power cycle. In one or more embodiments, the mixing zone 215 can be operated at pressures from about 100 psig to about 550 psig. In one or more embodiments, the mixing zone 215 can be operated at pressures from about 100 psig to about 450 psig. In one or more embodiments, the mixing zone 215 can be operated at pressures from about 100 psig to about 350 psig.

In one or more embodiments, the syngas produced in the gasifier 200 can include carbon monoxide, hydrogen, oxygen, hydrocarbons, sulfur, solids, mixtures thereof, derivatives thereof or combinations thereof. In one or more embodiments, the syngas produced in the gasifier 200 can be essentially nitrogen-free. In one or more embodiments, the process converts at least about 85%, or 90%, or 95%, or 98%, or 99% of the carbon from the feedstock to syngas.

In one or more embodiments, the syngas produced in the gasifier 200 can contain about 5% vol to about 50% vol carbon monoxide. In one or more embodiments, the syngas can contain about 15% vol to about 40% vol carbon monoxide. In one or more embodiments, the syngas can contain about 20% vol to about 30% vol carbon monoxide.

In one or more embodiments, the syngas can contain about 5% vol to about 25% vol hydrogen. In one or more embodiments, the syngas can contain about 10% vol to about 25% vol hydrogen. In one or more embodiments, the syngas can contain about 10% vol to about 20% by vol. hydrogen.

In one or more embodiments, the syngas can contain about 0.5% vol to about 3.0% vol nitrogen. In one or more embodiments, the syngas can contain about 0.5% vol to about 2.0% vol nitrogen. In one or more embodiments, the syngas can contain about 1.5% vol to about 3.0% vol nitrogen.

In one or more embodiments, the syngas can contain about 1% vol to about 20% vol methane. In one or more embodiments, the syngas can contain about 5% vol to about 15% vol methane. In one or more embodiments, the syngas can contain about 5% vol to about 10% vol methane.

In one or more embodiments, the syngas can contain less than about 30% vol carbon dioxide. In one or more embodiments, the syngas can contain less than about 25% vol carbon dioxide. In one or more embodiments, the syngas can contain less than about 20% vol carbon dioxide. In one or more embodiments, the syngas can contain less than about 15% vol carbon dioxide. In one or more embodiments, the syngas can contain less than about 10% vol carbon dioxide.

In one or more embodiments, the synthesis gas leaving the gasifier 200 can have a heating value, corrected for heat losses and dilution effects, of about 50 Btu/scf to about 75 Btu/scf, or about 50 Btu/scf to about 100 Btu/scf, or about 50 Btu/scf to about 110 Btu/scf, or about 50 Btu/scf to about 140 Btu/scf, or about 50 Btu/scf to about 180 Btu/scf, or about 50 Btu/scf to about 200 Btu/scf, or about 50 Btu/scf to about 250 Btu/scf, or about 50 Btu/scf to about 275 Btu/scf.

Steam can be supplied to the gasifier 200 to control the hydrogen to carbon monoxide ratio (H2:CO) within the gasifier 200. Since the outlet temperature of the gasifier 200 is proportionately less than comparable gasifiers (i.e. slag type), the amount of thermal heat versus chemical heat in the syngas is comparably less in the gasifier 200. Therefore, steam can be used to adjust by shift the H2:CO ratio with a smaller energy penalty than other entrained flow gasifiers operating at higher temperatures. Because of the reduced operating temperature within the gasifier (i.e. less than 2,900° F.), less energy is consumed to control and optimize the H2:CO ratio, thus the production of hydrogen can be increased without a commensurate increase in steam demand within the gasifier 200. For example, the synthesis gas leaving the gasifier 200 can have a H2:CO of at least 0.2. In one or more embodiments, the H2:CO ratio is at least 0.5. In one or more embodiments, the H2:CO ratio is about 0.25 to about 2.5. In one or more embodiments, the H2:CO ratio is about 0.4 to about 2.0. In one or more embodiments, the H2:CO ratio is about 0.5 to about 1.5. In one or more embodiments, the H2:CO ratio is about 0.8 to about 1.0.

Figure 3:
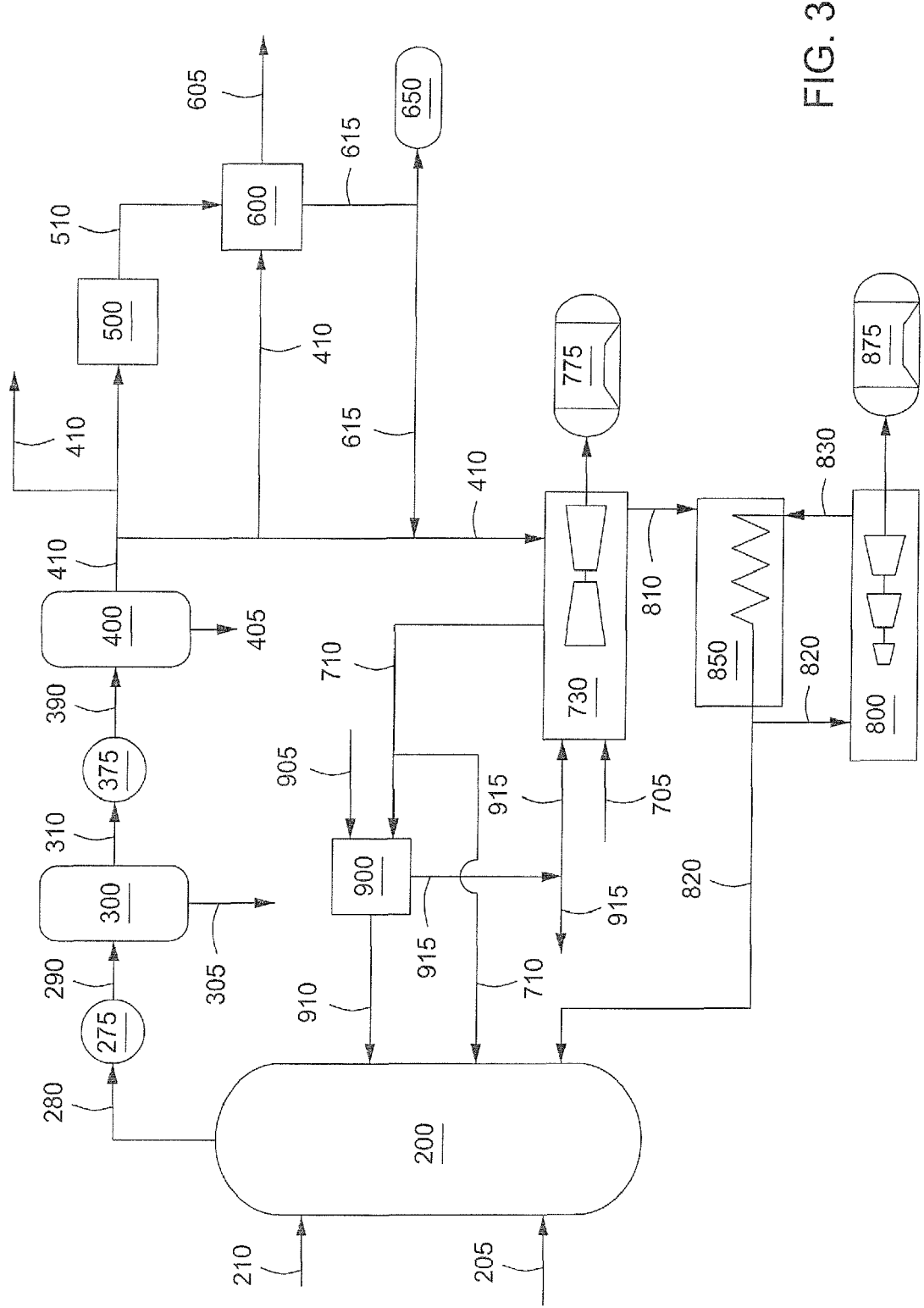
FIG. 3 depicts another illustrative gasification system according to one or more embodiments.

FIG. 3 depicts another illustrative gasification system according to one or more embodiments. In one or more embodiments, the gasification system can include one or more integrated combustion turbines 730 to further enhance efficiency. The one or more gasifiers 200, particulate removal systems 300, gas treatment systems 400, gas converters 500, hydrogen separators 600, steam turbines 800, heat recovery systems 850, generators 775, 875, and air separation units 900 can be the same as described above.

In one or more embodiments, at least a portion of the synthesis gas stream 410 can be combined with at least a portion of the hydrogen rich stream 615 to provide a fuel gas for the one or more combustion turbines 730. The combustion turbines 730 can produce a high temperature exhaust gas (stream 810) and shaft power to drive the one or more generators 775. In one or more embodiments, heat from the combustion turbine exhaust gas stream 810 (generally about 1100° F.) can be recovered using one or more heat recovery systems 850 to generate steam (stream 820) for subsequent use in a steam turbine 800, which can provide shaft power to drive the one or more generators 875. Lower pressure steam from the stream turbine 800 can be returned (via stream 830) to the heat recovery system 850.

In one or more embodiments, the heat recovery system 850 is a closed-loop heating system, e.g. a waste heat boiler, shell-tube heat exchanger, and the like, capable of exchanging heat between the higher temperature exhaust gas (via stream 810) and the lower pressure steam (stream 830) to produce higher pressure steam (stream 820). The heat recovery system 850 can provide up to 1500 psig, 1,000° F. superheat/reheat steam without supplemental fuel.

In one or more embodiments, ambient air via stream 705 can be drawn into the combustion turbine 730 to provide compressed air via stream 710 directly to the gasifier 200 and/or ASU 900. In one or more embodiments, nitrogen separated within the ASU 900 can be purged and/or returned to the one or more combustion turbines 730 (stream 915) to reduce NOx emissions by lowering the combustion temperature in the combustion turbine 730. The nitrogen acts as a diluent with no heating value, i.e. a heat sink. To further minimize NOx formation, the syngas stream 410 entering the combustion turbine(s) 730 can be saturated with water (not shown).

At least a portion of the high-pressure steam within stream 820 can be introduced to the one or more gasifiers 200, and/or other auxiliary steam consuming process equipment (not shown). In one or more embodiments, residual heat from stream 820 can be rejected to a condensation system well known to those skilled in the art or sold to local steam consumers.

Figure 4:
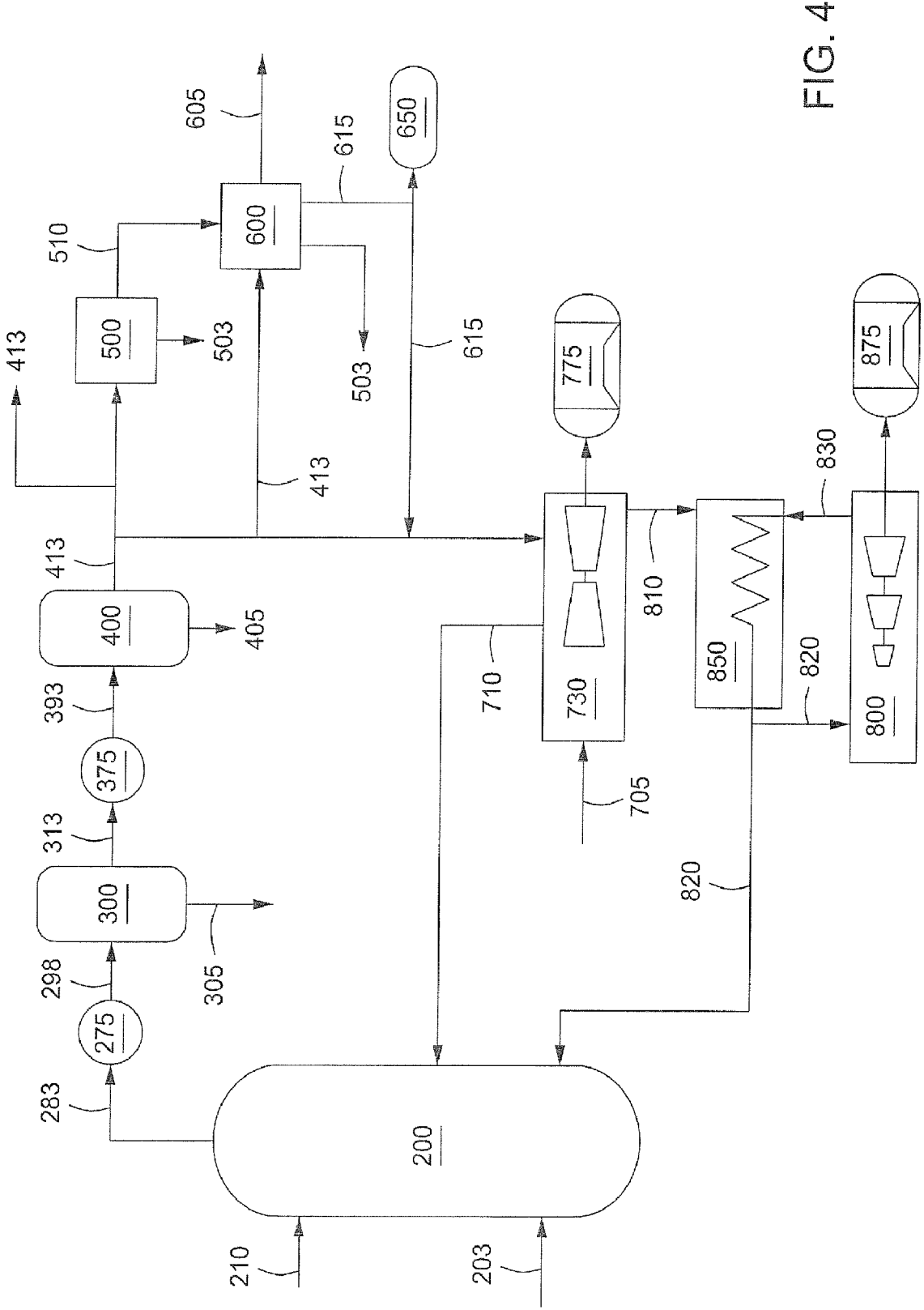
FIG. 4 depicts yet another illustrative gasification system according to one or more embodiments.

FIG. 4 depicts yet another illustrative gasification system according to one or more embodiments. The illustrative gasification system utilizes a nitrogen-containing oxidant stream 203 for gasification. The one or more nitrogen-containing oxidants in stream 203 can include air; oxygen-enriched air; mixtures of oxygen and air; mixtures of oxygen and nitrogen; and the like. In one or more embodiments, the nitrogen-containing oxidant can contain about 20% vol. or greater oxygen, or about 25% vol or greater oxygen, or about 30% vol. or greater oxygen. In one or more embodiments, the nitrogen-containing oxidant can contain at least 5 vol % nitrogen. In one or more embodiments, the nitrogen content of the nitrogen-containing oxidant can range from a low of about 5 vol %, 10 vol %, or 20 vol % to a high of about 25 vol %, 50 vol %, or 80 vol %.

In one or more embodiments, a raw syngas stream 283 containing one or more particulates and nitrogen can be cooled using the one or more coolers 275 to provide a cooled raw syngas stream 298. The one or more particulate removal systems 300 can be used to partially or completely remove the particulates from the cooled raw syngas stream 298 to provide a particulate stream 305 and a separated syngas stream 313. The separated syngas stream 313 can be cooled using the one or more secondary coolers 375 to provide a cooled, separated syngas stream 393. The cooled, separated syngas stream 393 can be treated within the one or more gas purification systems 400 to provide waste stream 405, and a treated syngas stream 413.

The treated syngas stream 413 that contains nitrogen can be converted within the one or more gas converters 500 to provide stream 510. In one or more embodiments, the one or more gas converters 500 can include cryogenic or membrane type systems for removing nitrogen from the treated syngas stream 413 to provide a Fischer-Tropsch feed stream containing HCN and NH3 in amounts of about 20 ppbv or less, or about 10 ppbv or less. The nitrogen removal systems can also be used to maintain the nitrogen concentration within the system. Nitrogen can be recovered and/or purged from the system via stream 503.

At least a portion of the converted gas stream 510 can be sold or upgraded using further downstream processes (not shown). In one or more embodiments, at least a portion of the converted gas stream 510 can be directed to the one or more hydrogen separators 600. In one or more embodiments, at least a portion of the treated syngas stream 413 can bypass the one or more gas converters 500 described above, and can be fed directly to the one or more hydrogen separators 600.

At least a portion of the hydrogen rich stream 615 can be used as a feedstock to one or more fuel cells 650, and at least a portion of the hydrogen rich stream 615 can be combined with the treated syngas stream 413 prior to use as a fuel in the one or more combustors 750. The hydrogen rich stream 615 can include varying amounts of nitrogen depending on the nitrogen content of the converted gas stream 510 and/or treated syngas stream 413.

In one or more embodiments, the hydrogen separators 600 can include at least one nitrogen separation unit to remove or at least substantially remove nitrogen, providing a nitrogen free or essentially nitrogen-free hydrogen rich stream 615, and/or nitrogen-free or essentially nitrogen-free, carbon dioxide rich stream 605. The separated nitrogen can be recovered and/or purged from the system via the stream 503.

In one or more embodiments, at least a portion of the synthesis gas stream 413 can be combined with at least a portion of the hydrogen rich stream 615 to provide a fuel gas for the one or more combustion turbines 730, which can provide shaft power to the one or more generators 775. In one or more embodiments, heat from the combustion turbine exhaust gas stream 810 (generally about 1100° F.) can be recovered using the one or more heat recovery systems 850 to generate steam (stream 820) for subsequent use in the steam turbine 800, which can provide shaft power to the one or more generators 875. Lower pressure steam from the stream turbine 800 can be returned (via stream 830) to the heat recovery system 850.

In one or more embodiments, ambient air via stream 705 can be drawn into the combustion turbine 730 to provide compressed air via stream 710 directly to the gasifier 200. Although not shown, the separated nitrogen via stream 503 can be purged and/or returned to the one or more combustion turbines 730 to reduce NOx emissions by lowering the combustion temperature in the combustion turbine 730. The nitrogen acts as a diluent with no heating value, i.e. a heat sink. To further minimize NOx formation, the syngas stream 413 entering the combustion turbine(s) 730 can be saturated with water (not shown).

At least a portion of the high-pressure steam within stream 820 can be introduced to the one or more gasifiers 200, and/or other auxiliary steam consuming process equipment (not shown). In one or more embodiments, residual heat from stream 820 can be rejected to a condensation system well known to those skilled in the art or sold to local steam consumers.

Any one or more of the above-described embodiments may be combined with another. The gasification system described provides an excellent balance in flexibility, efficiency and safety with low to no emissions. The gasifier in various embodiments operates at significantly higher circulation rates, velocities, and riser densities compared to other circulating or fluidized bed gasifiers. This results in higher throughput, better mixing, and increased heat and mass transfer rates. The gasifier also provides major efficiency improvements relative to slagging gasifiers as the slagging of coal ash requires a large amount of energy which cannot be recovered. In addition, non-slagging conditions are more conducive to long refractory life. Single stage operation provides still further efficiency gains. Other advantages over current gasifiers include high carbon conversion due to excellent gas/solids contact, and low water consumption, high percentage solids recirculation, high sulfur capture, high throughput, and high heat release rates that contribute to a small footprint as well as a simple mechanical design.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:

1. A process for producing electrical power, chemicals, carbon dioxide, and hydrogen, comprising:
    combining one or more feedstocks, carbon coated particulates, and oxidants in a fluidized reaction zone, wherein the one or more oxidants is present in an amount less than 5% of the stoichiometric amount of oxygen required for complete combustion of all the carbon introduced to the fluidized reaction zone, and wherein at least one of the one or more feedstocks comprises a polymer or plastic comprising a polyolefin;
    heating the reaction zone to a temperature of from about 600° F. to about 2,000° F. to provide a synthesis gas comprising carbon dioxide, of from about 10 vol % to about 85 vol % carbon monoxide, and of from about 1 vol % to about 50 vol % hydrogen;
    passing at least a portion of the synthesis gas to one or more turbines; and
    converting at least a portion of the synthesis gas to methanol, alkyl formates, dimethyl ether, ammonia, Fischer-Tropsch products, derivatives thereof, or combinations thereof.

2. The process of claim 1 wherein the synthesis gas is essentially nitrogen-free.

3. The process of claim 1 further comprising combining one or more sorbents containing limestone, dolomite or both with the feedstock and oxidant.

4. The process of claim 1 wherein the feedstock comprises coal which is ground to particles having an average particle diameter size ranging from 250 μm to 400 μm.

5. The process of claim 1 wherein the oxidant comprises at least 70 volume % oxygen.

6. The process of claim 1 wherein the oxidant comprises at least 70 volume % air.

7. The process of claim 1 wherein the feedstock comprises a coal based material selected from the group consisting of high-sodium lignite, low-sodium lignite, subbituminous coal, bituminous coal, and anthracite.

8. The process of claim 1 wherein the synthesis gas is fed on demand to the one or more turbines and gas converters.

9. A process for producing electrical power, carbon dioxide, and hydrogen, comprising:
    combining a feedstock comprising polymer, biomass, and coal with one or more oxidants and carbon coated particulates in a fluidized reaction zone heated from about 600° F. to about 2,000° F. to produce a synthesis gas comprising carbon dioxide, of from about 10 vol % to about 85 vol % carbon monoxide, and of from about 1 vol % to about 50 vol % hydrogen, wherein the polymer is selected from the group consisting of polypropylene, polyethylene, polystyrene, polyethylene terephthalate (PET), poly blends, other polyolefins, and poly-hydrocarbons limited to oxygen as an additional constituent, and wherein the one or more oxidants is present in an amount less than 5% of the stoichiometric amount of oxygen required for complete combustion of all the carbon introduced to the fluidized reaction zone;
    passing all or a portion of the synthesis gas to one or more turbines; and
    passing all or a portion of the synthesis gas to one or more gas converters to produce hydrogen, methanol, alkyl formates, dimethyl ether, ammonia, Fischer-Tropsch products, derivatives thereof, or combinations thereof.

10. The process of claim 9 wherein the synthesis gas is essentially nitrogen-free.

11. The process of claim 9 further comprising adding sorbent to the reaction zone, the sorbent comprising limestone, dolomite, or a combination thereof.

12. The process of claim 9 wherein the coal is ground to particles having an average particle diameter size ranging from 150 μm to 450 μm.

13. The process of claim 9 wherein the polymer is ground to particles having an average particle diameter size ranging from 150 μm to 450 μm.

14. The process of claim 9 wherein prior to heating, coke breeze is fed to the reaction zone and heated to a temperature of from 950° F. to 1200° F.

15. The process of claim 9 wherein the coal is selected from the group consisting of high-sodium lignite, low-sodium lignite, subbituminous coal, bituminous coal and anthracite.

16. The process of claim 9 wherein the oxidant comprises at least 70 volume % oxygen.

17. The process of claim 9 wherein the oxidant comprises at least 70 volume % air.

18. The process of claim 9 wherein at least one of the one or more combustion turbines is part of a combined cycle system.

19. The process of claim 9 wherein at least one of the one or more combustion turbines is part of an Integrated Gasification Combined Cycle.

20. A process for producing electrical power, chemicals, carbon dioxide, and hydrogen, comprising:
   combining a feedstock comprising plastic, coal, and ash with carbon coated particulates and one or more oxidants in a fluidized reaction zone at a temperature of about 600° F. to about 2,000° F., wherein the plastic comprises polypropylene, polyethylene, polystyrene, derivatives thereof or combinations thereof, and wherein the amount of the one or more oxidants is present in an amount less than 5% of the stoichiometric amount of oxygen required for complete combustion of all the carbon introduced to the fluidized reaction zone;
   producing one or more synthesis gas streams comprising carbon dioxide, of from about 10 vol % to about 85 vol % carbon monoxide, and of from about 1 vol % to about 50 vol % hydrogen;
   passing at least a portion of the one or more synthesis gas streams to one or more turbines; and
   passing at least a portion of the one or more synthesis gas streams to one or more gas converters to produce methanol, alkyl formates, dimethyl ether, ammonia, Fischer-Tropsch products, derivatives thereof, or combinations thereof.

21. The process of claim 20 wherein the synthesis gas streams are essentially nitrogen-free.

22. The process of claim 20 further comprising combining one or more sorbents containing limestone, dolomite or both with the coal and oxidant.

23. The process of claim 20 wherein the oxidant comprises at least 70 volume % oxygen.

24. The process of claim 20 wherein the oxidant comprises at least 70 volume % air.

25. The process of claim 20 wherein the coal based feedstock is selected from the group consisting of high-sodium lignite, low-sodium lignite, subbituminous coal, bituminous coal, and anthracite.

26. The process of claim 20 wherein the synthesis gas stream is fed on demand to the combustion turbine and gas converter.

27. A process for producing electrical power, chemicals, carbon dioxide, and hydrogen, comprising:
   combining a plastic, a coal based feedstock, carbon coated particulates, and nitrogen-containing oxidant in a fluidized reaction zone, wherein the amount of oxidant in the nitrogen-containing oxidant is less than 5% of the stoichiometric amount of oxygen required for complete combustion of all the carbon introduced to the fluidized reaction zone, and wherein the plastic comprises polypropylene, polyethylene, polystyrene, derivatives thereof, or combinations thereof;
   heating the reaction zone to a temperature of about 600° F. to about 2,000° F. to provide a synthesis gas stream comprising carbon dioxide, of from about 10 vol % to about 85 vol % carbon monoxide, nitrogen, and of from about 1 vol % to about 50 vol % hydrogen;
   passing at least a portion of the synthesis gas stream to one or more turbines; and
   converting at least a portion of the synthesis gas stream to produce methanol, alkyl formates, dimethyl ether, ammonia, Fischer-Tropsch products, derivatives thereof, or combinations thereof.

28. The process of claim 27 further comprising combining one or more sorbents containing limestone, dolomite or both with the coal and oxidant.

29. The process of claim 27 wherein the coal is ground to particles having an average particle diameter size ranging from 250 μm to 400 μm.

30. The process of claim 27 wherein the coal based feedstock is selected from the group consisting of high-sodium lignite, low-sodium lignite, subbituminous, bituminous, anthracite, and combinations thereof.

31. The process of claim 27 wherein the synthesis gas stream is fed on demand to the combustion turbine.

32. The process of claim 27 further comprising passing air from the combustion turbine through an air separation unit to produce an essentially nitrogen-free stream and recycling at least a portion of the essentially nitrogen-free stream to the reaction zone.

33. A process for producing electrical power, chemicals, carbon dioxide, and hydrogen, comprising:
   combining one or more feedstocks comprising one or more carbonaceous materials with carbon coated particulates, and one or more oxidants in a fluidized reaction zone, wherein the amount of the one or more oxidants is present in an amount less than 5% of the stoichiometric amount of oxygen required for complete combustion of all the carbon introduced to the fluidized reaction zone, and wherein at least one of the one or more feedstocks further comprises a polymer or plastic selected from the group consisting of polypropylene, polyethylene, polystyrene, derivatives thereof, and combinations thereof;
   heating the reaction zone to a temperature of from about 600° F. to about 2,000° F. to produce errant oxygen, carbon dioxide, of from about 10 vol % to about 85 vol % carbon monoxide, and of from about 1 vol % to about 50 vol % hydrogen; and
   adding one or more materials capable of absorbing or consuming the errant oxygen at a rate and level sufficient to delay or prevent the errant oxygen from reaching a concentration sufficient to support uncontrolled reactions with the hydrogen.

34. The process of claim 33 further comprising combining one or more sorbents containing limestone, dolomite or both with the one or more feedstocks and oxidants.

35. The process of claim 33 wherein the carbonaceous material is ground to particles having an average particle diameter size ranging from 250 μm to 400 μm.

36. The process of claim 33 wherein the feedstock is selected from the group consisting of high-sodium lignite, low-sodium lignite, subbituminous coal, bituminous coal, and anthracite.

37. The process of claim 33 wherein the one or more materials capable of absorbing or consuming the errant oxygen comprises carbon rich ash.

38. The process of claim 37 wherein the carbon rich ash circulates within the fluidized reaction zone.

39. The process of claim 33 wherein the errant oxygen enters the fluidized reaction zone during an interruption of the feedstock feed.

40. The process of claim 1, wherein the polyolefin comprises polyethylene or polypropylene.

41. The process of claim 1, wherein the polyolefin comprises polystyrene.

42. The process of claim 1, wherein the polyolefin comprises polyethylene terephthalate (PET).

43. The process of claim 9, wherein the polymer is polyethylene.

44. The process of claim 9, wherein the polymer is polypropylene.

45. The process of claim 9, wherein the polymer is polystyrene.

46. The process of claim 20, wherein the plastic is polyethylene.

47. The process of claim 20 wherein the plastic is polypropylene.

48. The process of claim 20 wherein the plastic is polystyrene.

49. The process of claim 27, wherein the plastic is polyethylene.

50. The process of claim 27, wherein the plastic is polypropylene.

51. The process of claim 27, wherein the plastic is polystyrene.

52. The process of claim 33, wherein the polymer or plastic comprises polyethylene.

53. The process of claim 33, wherein the polymer or plastic comprises polypropylene.

54. The process of claim 33, wherein the polymer or plastic comprises polystyrene.

* * * * *